United States Patent [19]
Brown, Jr.

[11] Patent Number: 5,921,396
[45] Date of Patent: *Jul. 13, 1999

[54] SPECIMEN COLLECTION KIT FOR MAILING AND METHOD OF USING SAME

[76] Inventor: Jacob T. Brown, Jr., 2 N. Charles St., Suite 910, Baltimore, Md. 21201

[ * ] Notice: This patent issued on a continued prosecution application filed under 37 CFR 1.53(d), and is subject to the twenty year patent term provisions of 35 U.S.C. 154(a)(2).

[21] Appl. No.: 08/787,493

[22] Filed: Jan. 21, 1997

[51] Int. Cl.$^6$ ................................................. B65D 69/00
[52] U.S. Cl. ........................... 206/569; 206/570; 206/223
[58] Field of Search ................................... 206/223, 438, 206/569, 570, 571, 572, 459.5

[56] References Cited

U.S. PATENT DOCUMENTS

| | | |
|---|---|---|
| 4,122,947 | 10/1978 | Falla .................................... 206/569 |
| 4,128,954 | 12/1978 | White .................................. 206/459.5 |
| 4,240,547 | 12/1980 | Taylor .................................. 206/569 |
| 4,860,899 | 8/1989 | McKee ................................. 206/534 |
| 4,917,238 | 4/1990 | Schumacher ........................ 206/572 |
| 4,927,405 | 5/1990 | Martin et al. ....................... 206/569 |
| 4,985,232 | 1/1991 | Jacobssen ........................... 206/569 |
| 5,046,609 | 9/1991 | Mangini et al. .................... 206/459.5 |
| 5,161,687 | 11/1992 | Kornell et al. ..................... 206/459.5 |
| 5,186,900 | 2/1993 | Jensen et al. ....................... 206/569 |
| 5,388,699 | 2/1995 | Ratajczak et al. ................. 206/569 |
| 5,589,137 | 12/1996 | Markin et al. ...................... 206/569 |

Primary Examiner—David T. Fidei
Attorney, Agent, or Firm—Millen, White, Zelano & Branigan, P.C.

[57] ABSTRACT

A combination clinical specimen collection kit and shipping means, including packaging components, is provided, which is uniquely adapted and acceptable for shipment and delivery through regular first-class mailing-delivery systems, for both domestic and overseas purposes. The kit includes two vials and a rectangular cushion block having two cylindrical recesses for receiving the vials.

15 Claims, 5 Drawing Sheets

SPECIMEN COLLECTION KIT FOR MAILING AND METHOD OF USING SAME

CROSS-REFERENCE TO RELATED PATENT

This application is related to U.S. Pat. No. 4,949,840, issued Aug. 21, 1990, which is incorporated by reference herein.

FIELD OF THE INVENTION

The present invention is related to the field of drug abuse screening and laboratory testing, and more particularly to individual clinical specimen collection kits for mailing liquid samples or specimens of body fluids, such as urine, through the regular U.S. mail service system from points of origin to remote laboratory test and analysis facilities.

BACKGROUND OF THE INVENTION

In the prior art, hospitals, clinics and doctors, etc., have routinely taken various samples or specimens of a patient's blood, urine or stool and the like, to be sent for testing and analysis by an outside remote laboratory. Such specimens must be transported and delivered promptly to such laboratories by means which will not cause damage or spillage thereto. Present widely employed delivery packages may include a glass test tube or plastic vials as containers for such specimen collection. Once closed, the container is deposited in a small cardboard cylindrical packaging/delivery tube, usually no larger than ½ inch to 2 inches in diameter and no longer than 6 inches. Generally, the inserted container is loosely surrounded by various types of packaging materials, such as newspaper, foam rubber, etc., for the purpose of inhibiting the container's movement within the cardboard tube. The cardboard tube may have metal end pieces or metal screw-on caps to retain the container within the packaging tube.

Such a package ready for transport and delivery is rather weighty and bulky, and costly for shipment via the regular first-class U.S. mail service system, and, therefore, is undesirable for mass or individual mailings as may be required in connection with extensive mailings associated with various drug testing programs which have impact on a significant percentage of the nation's current population.

Recently, the Supreme Court of the United States has ruled that transportation operators, such as railroads, airlines, buses and the like may require testing for drug abuse of its employees. In addition, many employers have instituted private programs for testing their employees. Further, many parents have expressed concern about the widespread use by school age children and many have expressed a desire for individual means whereby they could test and monitor whether their children are involved in any drug abuse activities.

It is difficult to predict how extensive the need or desire for such drug testing will grow. However, one thing is certain: drug abuse has reached into almost every area of business and society of this nation. Thus, private industry, governmental agencies and private individuals alike, have serious concerns and will seek the assistance of various testing and evaluation laboratories to analyze samples and specimens for drug abuse on an ever expanding basis.

As a consequence of the anticipated escalation in the volume of packages which may be required or desirable to be sent through the mail service system, it has therefore become paramount to provide a lightweight and inexpensive transport and delivery package adapted and acceptable for use in mailing body fluid specimens to remote laboratories for drug testing and analysis, which is cost effective.

The prior art packaging and process shipping and delivery via the current mail service system have several undesirable features either singularly or in combination; namely, that there are no mechanical or structural means immediately surrounding the specimen carrying container to insure that the plug or cap of said vial will not become unplugged; nor is there provided specific means for absorption of fluid specimen in the unlikely event of the leakage or rupture of the container; nor is there provided further shock absorption means to minimize, if not eliminate, damage to the specimen carrying container in transit; and last and more importantly, the complete shipping and delivery package of the prior art is not an economical and cost effective means in view of the significantly high cost of shipping, both domestically and overseas, via the current first-class mail service system, which is used for prompt delivery of such test specimens.

U.S. Pat. No. 4,949,840 addresses this problem; however, since the issuance of this patent, improvements have been made over the kit and method disclosed in this patent.

SUMMARY OF THE INVENTION

It is a feature of the present invention to provide a shipping and delivery package and method of using the same which is economical, convenient and readily adaptable for use in the mail.

In view of this object and other objects, the present invention is directed to an improved animal body fluid specimen collection kit for mailing via regular mail service system, wherein the improvement comprises a pair of vials, a foldable urine collection cup, a cushion block with two bores therein for retaining the vials, a sealable pouch for containing the block and a mailing envelope which is sealable for mailing an assembly of the two vials, cushion block and sealing pouch.

In a further aspect of the invention, the vials each have identical identifying codes thereon and screw tops.

In still a further aspect of the invention, the foam block is rectangular in cross section.

In still a further aspect of the invention, the block includes an absorbent wipe for cleaning the exterior of the vials once the vials have been filled.

In accordance with a method of practicing the invention, two specimen collection vials are at least partially filled with a urine sample. The containers are then closed with caps and inserted in a block of cushioning material. The block of cushioning material is then inserted into a pouch which is thereafter sealed and the pouch is placed in a mailing container which is thereafter sealed. The mailing container is then mailed to a laboratory where the urine sample in the vials is tested for the presence of at least one selected material or a plurality of selected materials.

In still a further aspect, the at least one selected material is marijuana, opiates, cocaine, PCP or an amphetamine or any other substance of abuse.

In still a further aspect, the method is used to test for a plurality of the above-identified types of materials.

BRIEF DESCRIPTION OF THE DRAWINGS

Various other features and attendant advantages of the present invention will be more fully appreciated as the same becomes better understood when considered in conjunction with the accompanying drawings, in which like reference characters designate the same or similar parts throughout the several views, and wherein.

DETAILED DESCRIPTION

The Kit (FIGS. 1–6)

Figure 1:
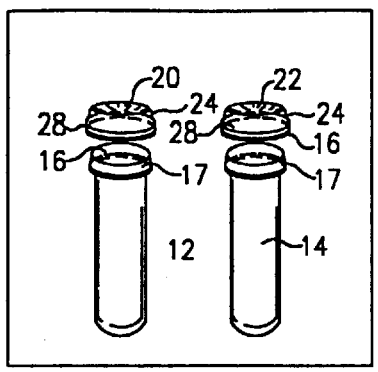
FIG. 1 is a perspective view of a pair of vials for receiving a sample of urine.

Referring now to FIGS. 1–6, the components of a kit 10 are shown separately. It is to be kept in mind that these components are packaged together to form a kit to be utilized in accordance with the method of the present invention. FIG. 1 shows the vials 12 and 14. The two vials 12 and 14 have a capacity 12 cc. The vials each have an open top end 16 with a helical thread 17. The vials 12 and 14 are closed by screw caps 20 and 22, each of which have a circular flange portion 24 with an internal thread 28 that threadably engages the external threads of vials 12 and 14. Preferably, the vials 12 and 14, as well as the caps 20 and 22, are transparent.

Figure 2:
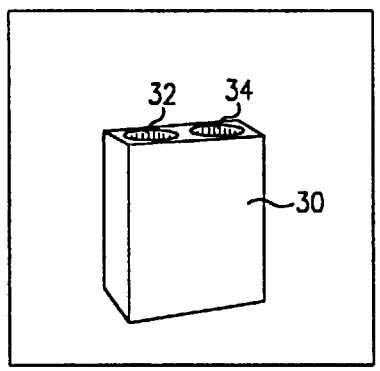
FIG. 2 is a block of cushion material for receiving the vials of FIG. 1.

Referring now to FIG. 2, there is shown a block of cushioning material 30. The block of cushioning material 30 has two circular recesses 32 and 34 therein for receiving the vials 12 and 14. Preferably, the cushioning material is made of a foam material such as polypropylene foam or polystyrene foam. The block of FIG. 2 is preferably rectangular in cross section.

Figure 3:
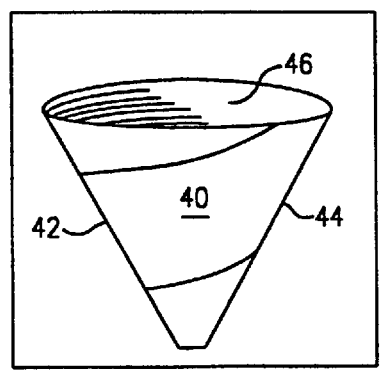
FIG. 3 is a foldable paper cup for collecting the urine sample used with the vials of FIG. 1.

Referring now to FIG. 3, there is shown a urine collection cup 40. Preferably, the urine collection cup 40 is conical in shape and is packaged flat with the edges 42 and 43 forming seams. When the seams are hand squeezed together, the cup 40 opens to provide a urine collection space 46.

Figure 4:
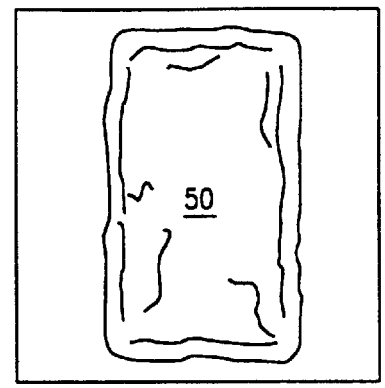
FIG. 4 is a planar view of an absorbent wipe used to clean the vials of FIG. 1.

Referring now to FIG. 4, there is shown an absorbent wipe 50. The absorbent wipe 50 is preferably rectangular and is made of a cellulose material so it can be easily disposed of.

Figure 5:
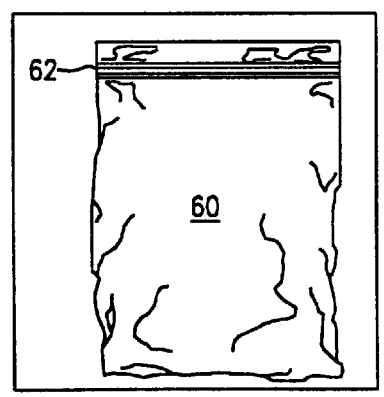
FIG. 5 is a planar view of a zip-lock pouch which contains an assembly of the vials of FIG. 1 and block of FIG. 2.

Referring now to FIG. 5, there is shown a pouch 60. The pouch 60 is transparent so that its contents are readily discernible and includes a ZIP-LOCK® rib-in-slot closure 62 which seals the bag 60.

Figure 6:
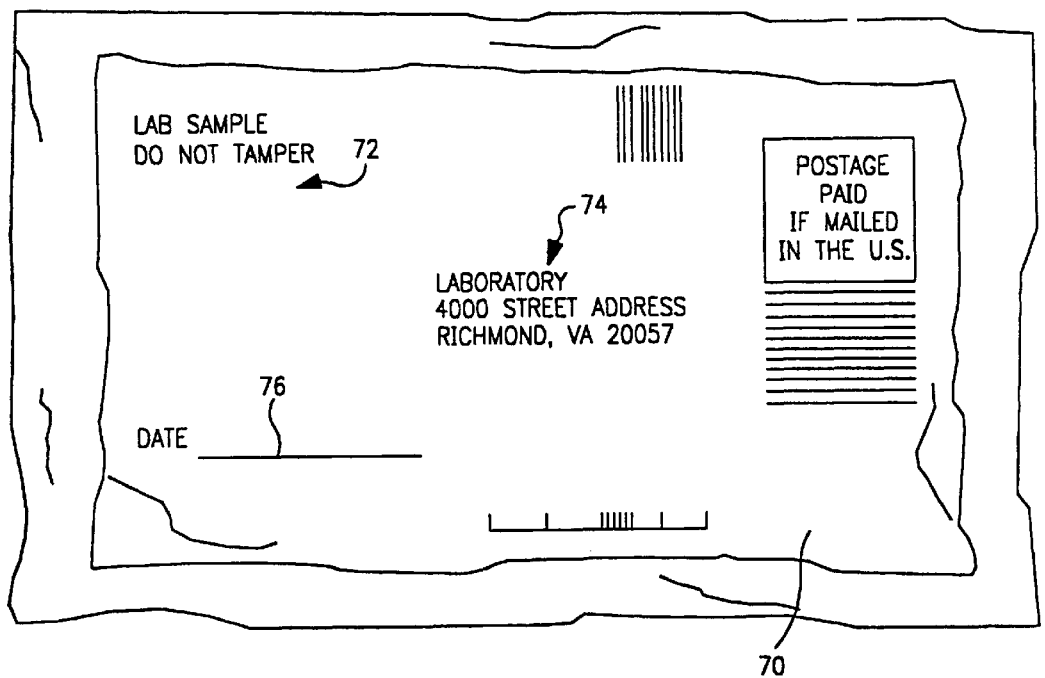
FIG. 6 is a front view of a mailing envelope in which the sealed pouch of FIG. 5 is inserted for mailing to a central laboratory at which the urine samples in the vials are analyzed.
Figure 7:
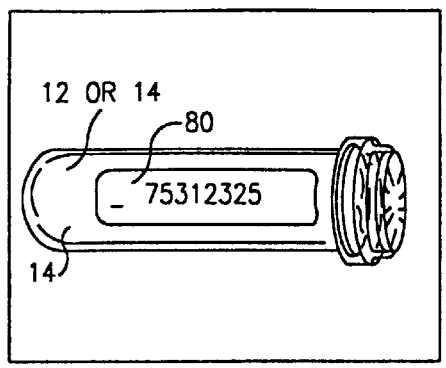
FIG. 7 is a side view of one vial.

Referring now to FIG. 6, there is a front view of a standard bubble bag 70 which is a mailing envelope approved by the United States Postal Service and which is used to mail the assembly of the pouch 60 containing the polypropylene cushion block 30 and vials 12 and 14 which are received in the cylindrical recesses 32 and 34 in the block 30. The standard mailing envelope 70 includes indicia thereon which includes a warning 72 that it is a lab sample and should not be opened, the address of the laboratory 74 and a date line 76. The date on the date line 76 is the date that the sample is taken and not some other date such as the mailing date which should appear on the postmark.

The Method of Practicing the Invention Using the Kit 10 (FIGS. 7–21)

Referring now to FIGS. 7–21, where the method of practicing the invention is illustrated, it is seen that the vials 12 and 14 each have an identical identifying indicia, such as a number 80, thereon. There are two vials, each having a capacity of about 12 cc, so that a total urine sample of about 24 cc may be collected. This provides sufficient volume for an accurate test. Hence, each vial of a kit has an identical identifying number 80 which is electronically scanned at a laboratory. Consequently, the chances of a mistake being made due to samples being in some way interchanged is minimized. Moreover, the number 80 serves as a code to preserve the confidentiality of the sample and the test results. The vials 12 and 14 are made of a non-contaminating material and are transparent so that the person pouring the urine sample therein can readily determine how full the vials are. Preferably, the vials 12 and 14 are not filled all the way to the top, but are filled in the range of about 75% to 90%. Moreover, the vials 12 and 14 are about 2½ inches high and have a diameter of about ½ inch and are made of a shatter-proof plastic that is non-contaminating.

Figure 10:
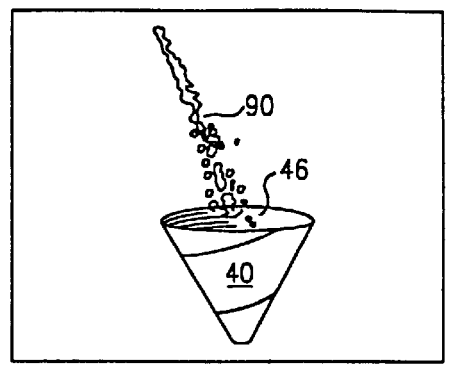
FIG. 10 is a perspective view of a urine sample being collected in the cup.
Figure 8:
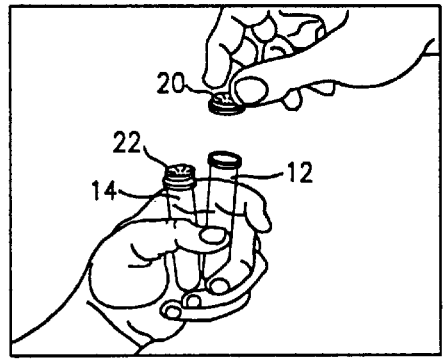
FIG. 8 is a perspective view showing vials being uncapped.
Figure 9:
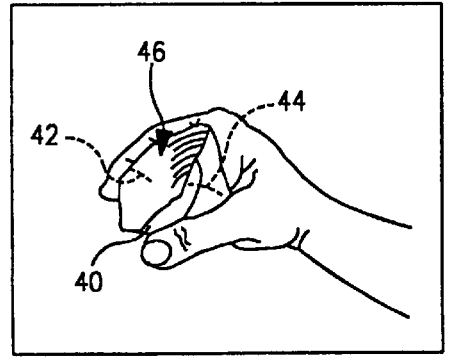
FIG. 9 is a perspective view showing a paper cup being opened.

Referring now to FIG. 8, it is seen that the vials 12 and 14 of the kit 10 come capped in order to avoid contamination. As is seen in FIG. 9, the first step in the method of using kit 10 is to squeeze the cup 40 at the seams 42 and 44 so that the cup opens to provide the urine sample space 46. Referring now to FIG. 10, the cup 40 is shown being filled with urine sample 90 from a urine stream 92.

Figure 11:
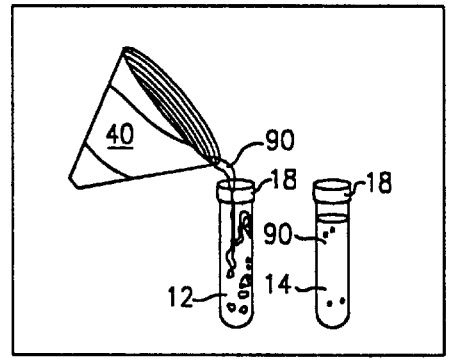
FIG. 11 is a perspective view showing the vials being filled with urine.

In FIG. 11, the vials 12 and 14 are shown being filled with the urine sample 90 from the cup 40. It is important that the vials 12 and 14 be filled from the cup 40 instead of directly with a stream of urine 92 because the vials would be more likely to overflow if filled directly.

Figure 12:
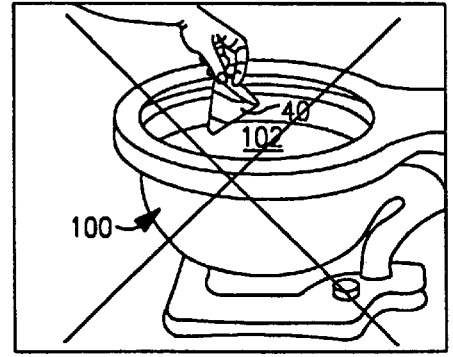
FIG. 12 is a perspective view illustrating that the fluid sample is not to be filled with water from a toilet in which the urine sample has been deposited.

As is seen in FIG. 12, it is important that the cup 40 not be filled from a toilet 100, since the urine from the toilet 100 will be diluted with water standing in the bowl 102 of the toilet.

Figure 13:
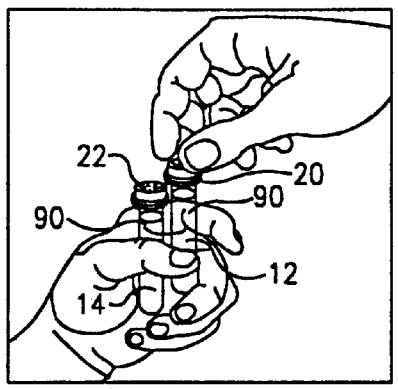
FIG. 13 is a perspective view showing the screw-on lids or caps being replaced.

Referring now to FIG. 13, the caps 20 and 22 are shown being screwed back on to the vials 12 and 14 to securely close the vials.

Figure 14:
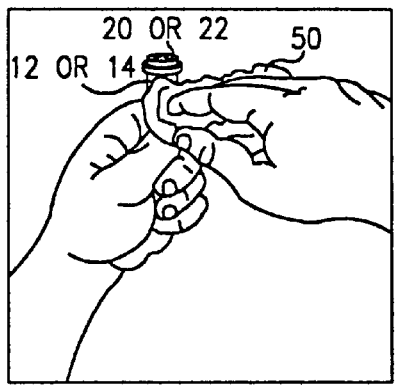
FIG. 14 is a perspective view showing one of the vials being cleaned with an absorbent wipe.

In FIG. 14, the wipe 50, which is made of a highly absorbent material and is part of the kit 10, is used to wipe the surfaces of the vials 12 and 14 remove any spillage of the vials. The wipe 50 is made of a highly absorbent material which is available from the Sealed Air Corporation, a concern having a New Jersey address.

Figure 15:
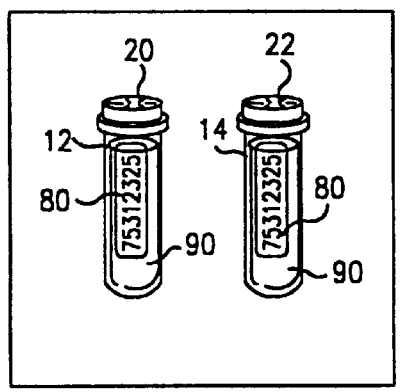
FIG. 15 is a side perspective view showing vials with a urine sample therein.

Referring now to FIG. 15, the vials 12 and 14 are shown filled with the urine sample 90 and closed with the screw-on caps 20 and 22.

Figure 16:
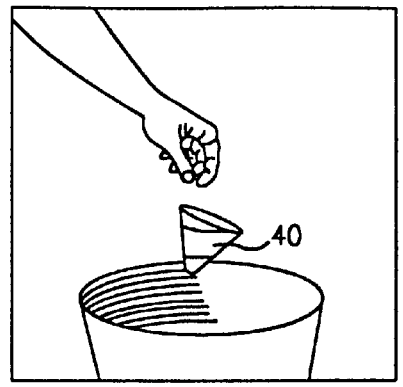
FIG. 16 is a perspective view showing that the paper cup is disposed in regular domestic trash.
Figure 17:
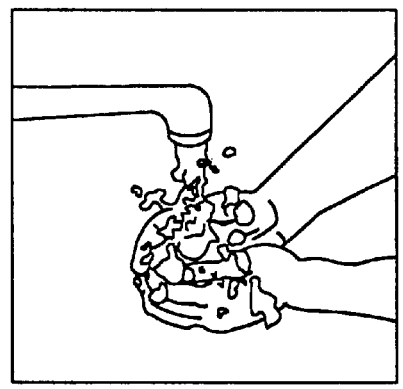
FIG. 17 is a perspective view showing a person who has handled the sample washing their hands.

Cleaning up from the procedure as practiced thus far in FIGS. 7–15 is shown in FIGS. 16 and 17, wherein the cup 40 and wipe 50 are thrown in a trash can and the hands of the person performing the procedures are washed (FIG. 17).

Figure 18:
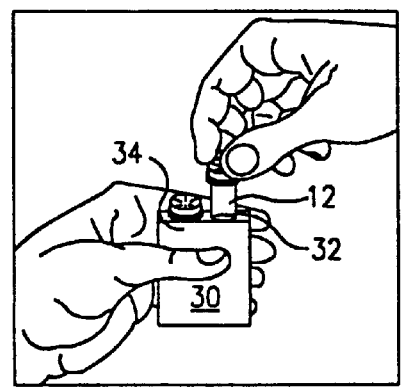
FIG. 18 is a perspective view showing the vials of FIG. 15 being inserted into the rectangular cushion block.

Packaging of the urine sample 90 is shown in FIGS. 18–21, wherein the vials 12 and 14 are inserted in the cylindrical recesses 32 and 34 of the block 30 of cushioning material (see FIG. 18).

Figure 19:
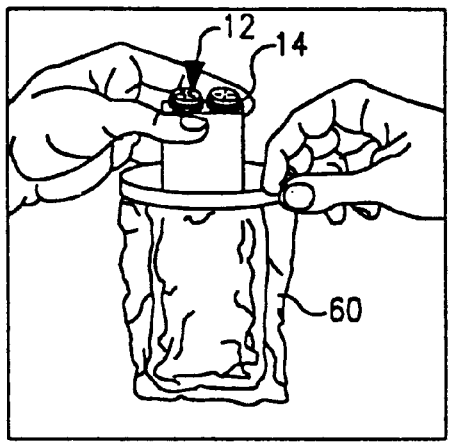
FIG. 19 is a side perspective view showing an assembly of the block and pair of vials being placed in zip-lock-type pouch.

In FIG. 19, the block of cushioning material 30 is shown inserted into the zip-lock pouch 60 of FIG. 19. The ZIP-LOCK® rib-in-slot closure 62 is then closed to retain the assembly of the cushioning material 30 and vials 12 and 14 therein.

Figure 20:
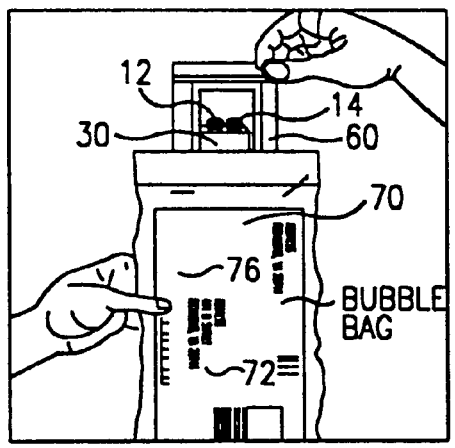
FIG. 20 is a perspective view showing the assembly of FIG. 19 with the pouch being closed and being inserted into a double bag-type mailing envelope.

In FIG. 20, the closed pouch 60 is inserted into the bubble bag envelope 70. The bubble bag envelope is of a size positioned to retain the filled pouch 60 and is a standard United States Postal Service mailing envelope (see FIG. 20). The envelope 70 may have dimensions of about 5 inches×8 inches.

Figure 21:
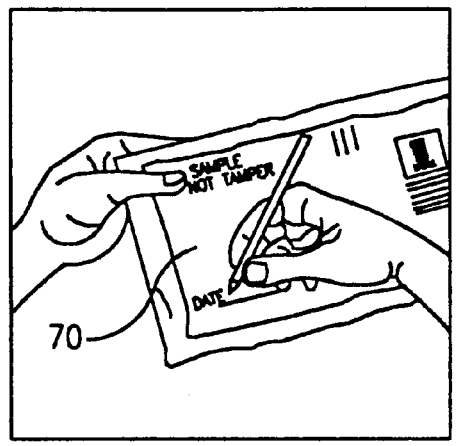
FIG. 21 is a perspective view showing the date that the sample was placed in the bag being written on the envelope.

Referring now to FIG. 21, after the envelope 70 has been sealed, the date that the urine sample identified by the number 80 was collected is written on line 76.

Figure 22:
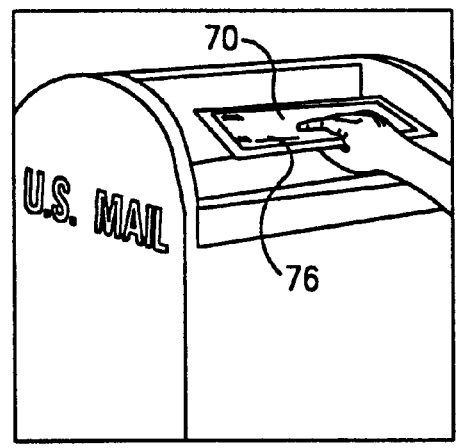
FIG. 22 is a perspective view showing the bubble bag mailing envelope being mailed to a laboratory.

In FIG. 22, the envelope 70 which contains the sample is shown being mailed to the laboratory (not shown) identified by the address 74 of FIG. 6. The laboratory (not shown) then communicates with the provider of the sample to inform the provider of the sample as to the results of the urine test.

A preferred use of the invention is by the parents of minors in situations where the parents are suspicious that the minor may be using a controlled substance such as one of the drugs identified in the Background of the Invention.

Other users may be employers, athletic teams or any other entity which might find drug testing by mail to be of value.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A kit for facilitating testing of urine of a person for drugs, wherein a urine sample is collected at a collection site remote from an analyzing site, which analyzing site analyzes urine samples collected at numerous urine collection sites, each kit comprising:

only two vials adapted to contain a urine sample from a single individual, each of the vials having substantially the same volume and having identifying indicia thereon specific to the person being tested, and each of the vials being about 2½ high and about ½ inch in diameter;

a pair of closures for the vials to close the vials with the urine sample therein;

a container for receiving the urine sample from the individual and for transferring the urine sample to the vials;

a block of protective foam material having only two circular recesses therein for receiving the vials with the urine sample therein for cushioning the vials;

a single flexible pouch with a fluid tight seal for receiving the block with the two urine filled vials therein; and a pre-addressed mailing envelope for receiving therein the flexible pouch with the vials and protective block contained within the flexible plastic pouch.

2. The kit of claim 1, further including an absorbent wipe.

3. The kit of claim 1, wherein the protective foam material is polypropylene foam.

4. The kit of claim 1, wherein the pre-addressed mailing envelope is about 8 inches long and about 5 inches wide.

5. The kit of claim 1, wherein the pouch has a rib-in-slot closure.

6. A system used for drug testing, the system comprising:

a central analyzing site for testing urine samples to determine the presence or absence of one or more drugs in those samples, the analyzing site having a mailing address and the capability of identifying a code assigned to each urine sample;

a number of drug testing kits, each drug testing kit having a different code for identifying by code an individual sample, each drug testing kit comprising:

only two vials for containing a urine sample from a single individual, each of the vials having substantially the same volume and a code thereon specific to the individual being tested, each vial being about 2½ inches high and about ½ inch in diameter;

a pair of closures for the vials to close the vials with the urine sample therein;

a collapsible container for receiving the urine sample from the individual and for transferring the urine sample to the two vials;

a block of protective foam material having two circular recesses therein for receiving the vials with the urine sample therein to cushion the vials;

a flexible plastic pouch with a fluid tight seal for receiving the protective block with the two urine filled vials therein; and a pre-addressed mailing envelope for receiving therein the flexible plastic pouch with the vials and protective block contained within the flexible plastic pouch.

7. The system of claim 6 further including an absorbent wipe for each kit.

8. The system of claim 6, wherein the collapsible container for each kit is a collapsible paper cup.

9. The system of claim 6, wherein the protective foam material is polypropylene foam.

10. The system of claim 6, wherein the pre-addressed mailing envelope is about 8 inches long and about 5 inches wide.

11. The system of claim 6, wherein the pouch has a rib-in-slot closure.

12. A method of drug testing, comprising:

distributing a multiplicity of drug testing kits, each having a number associated therewith, each kit comprising:

a container; only two vials of substantially the same volume, each of the two vials having a number thereon; caps for the vials; a block of cushioning material with two recesses therein, a single sealable pouch and a mailing envelope; and having at least some of the persons possessing a kit use the kit by:
- having a suspected user urinate directly into the container to collect a single urine sample, thereafter pouring the urine sample into the two vials to provide a single urine sample divided among two vials;
- inserting the two vials into the two recesses in the block of cushioning material;
- sealing the block of cushioning material in the pouch;
- inserting the pouch into the mailing envelope;
- mailing the pouch to testing laboratory;
- testing the urine sample in the two vials at the testing laboratory; and
- matching the results of the test with the number on the vials so that the results of the test can be communicated to a person knowing the number.

13. The method of claim 12 further including providing a disposable absorbent wipe with the kit for removing spillage.

14. The method of claim 12 further including posting the mailing envelope in a national post office.

15. The method of claim 12, wherein the container is configured as a collapsible paper cup.

* * * * *